United States Patent
Yasuda et al.

(10) Patent No.: US 9,372,141 B2
(45) Date of Patent: Jun. 21, 2016

(54) VISCOSITY MEASURING APPARATUS

(75) Inventors: Masanori Yasuda, Kyoto (JP); Keiji Sakai, Bunkyo-ku (JP)

(73) Assignee: Kyoto Electronics Manufacturing Co., Ltd., Kyoto (JP)

( * ) Notice: Subject to any disclaimer, the term of this patent is extended or adjusted under 35 U.S.C. 154(b) by 205 days.

(21) Appl. No.: 14/130,400

(22) PCT Filed: Jul. 20, 2012

(86) PCT No.: PCT/JP2012/068426
§ 371 (c)(1),
(2), (4) Date: Dec. 31, 2013

(87) PCT Pub. No.: WO2013/015211
PCT Pub. Date: Jan. 31, 2013

(65) Prior Publication Data
US 2014/0165710 A1  Jun. 19, 2014

(30) Foreign Application Priority Data
Jul. 27, 2011 (JP) ................................. 2011-163889

(51) Int. Cl.
*G01N 11/14* (2006.01)
*G01N 11/10* (2006.01)

(52) U.S. Cl.
CPC ................ *G01N 11/14* (2013.01); *G01N 11/10* (2013.01); *G01N 2011/147* (2013.01)

(58) Field of Classification Search
CPC ................ G01N 11/14; G01N 11/142; G01N 2011/147; G01N 2011/002; G01N 2203/0676
See application file for complete search history.

(56) References Cited

U.S. PATENT DOCUMENTS

| 5,533,800 | A | 7/1996 | Stiegelmann et al. |
| 2003/0033859 | A1* | 2/2003 | Schoeb ................ A61M 1/101 73/54.28 |

(Continued)

FOREIGN PATENT DOCUMENTS

| GB | 2417564 A | 3/2006 |
| JP | 57-12345 A | 1/1982 |

(Continued)

OTHER PUBLICATIONS

Bano et al. "A viscosity and density meter with a magnetically suspended rotor," Review of Scientific Instruments, Nov. 2003, vol. 74, No. 11, pp. 4788-4793.

*Primary Examiner* — Eric S McCall
*Assistant Examiner* — Mohammed E Keramet-Amircola
(74) *Attorney, Agent, or Firm* — Birch, Stewart, Kolasch & Birch, LLP

(57) ABSTRACT

A conductive rotator is immersed in a sample liquid in a sample container. A magnet is arranged at a specific distance from the rotation plane of the rotator in a direction of a rotating axis of the rotator so as to face the sample container. The magnet applies a magnetic field to the rotator from the outside of the sample container. A fluctuating magnetic field drive unit drives the magnet to apply the magnetic field that fluctuates in term of time to the rotator. Induced current is excited in the rotator by the fluctuating magnetic field. A rotating torque is provided to the rotator by the Lorenz interaction between the induced current and the fluctuating magnetic field, and as a result, the rotator rotates in the rotation plane. A viscosity detecting unit obtains the viscosity of the sample liquid based on a rotating state of the rotator and a time-fluctuating state of the fluctuating magnetic field.

17 Claims, 4 Drawing Sheets

(56) References Cited

U.S. PATENT DOCUMENTS

| | | | | |
|---|---|---|---|---|
| 2003/0154772 | A1* | 8/2003 | Jackson | G01N 11/14 73/54.28 |
| 2005/0087002 | A1* | 4/2005 | Kanzaki | B01F 13/0827 73/54.28 |
| 2010/0008182 | A1 | 1/2010 | Krusche et al. | |
| 2010/0071442 | A1* | 3/2010 | Moon, Jr. | G01N 11/14 73/54.28 |
| 2010/0116034 | A1* | 5/2010 | Abbott | G01N 11/14 73/54.35 |
| 2010/0121583 | A1* | 5/2010 | Abbott | G01N 11/14 702/50 |
| 2010/0162798 | A1* | 7/2010 | Gautsch | G01N 11/14 73/54.28 |
| 2011/0036150 | A1* | 2/2011 | Sakai | G01N 11/14 73/54.31 |
| 2013/0245968 | A1* | 9/2013 | Searle | G01N 11/14 702/50 |
| 2014/0047903 | A1 | 2/2014 | Sakai | |

FOREIGN PATENT DOCUMENTS

| | | |
|---|---|---|
| JP | 63-12936 A | 1/1988 |
| JP | 7-253388 A | 10/1995 |
| JP | 2007-136443 A | 6/2007 |
| JP | 2009-264982 A | 11/2009 |

* cited by examiner

VISCOSITY MEASURING APPARATUS

TECHNICAL FIELD

The present invention relates to a viscosity measuring apparatus for measuring viscosity of materials by means of a rotator.

BACKGROUND ART

Measuring viscosity of a material is an indispensable technique for quality control, performance evaluation, material control, research and development in manufacturing process of medicament, foods, coatings, inks, cosmetics, chemicals, papers, adhesives, fiber, plastics, beer, detergents, concrete admixture, and silicone or the like. As the methods of measuring the viscosity of such product, there is a method using a capillary tube, a method by making an oscillator contact a sample, a method using a rotator, and so on.

One of the methods using a rotator among the above-mentioned methods is disclosed in an after-mentioned Patent literature 1. The technique is configured so that a conductive rotator (sphere) is sank in a sample container containing a sample liquid, and a rotating magnetic field is given to the rotator from an outside of the sample container. At giving the rotating magnetic field, the electric current is excited in the rotator by the rotating magnetic field. The rotator rotates caused by the interaction of Lorentz force between the electric current and the rotating magnetic field is given to the rotator. At this time, the rotating speed of the rotator gets lower than the rotating speed of the rotating magnetic field according to the viscosity of the sample liquid. The viscosity can be calculated by means of such lag of the rotating speed. That is to say, a relation of the rotating speed of the rotator and the difference between the rotating speed of the rotator and the rotating speed of the rotating magnetic field can be expressed by a linear equation, and a slope of the linear equation becomes the viscosity.

CITATION LIST

Patent Literature

Patent Literature 1: Japanese Unexamined Patent Application Laid-open Publication No. 2009-264982

SUMMARY OF INVENTION

Technical Problem

The technique disclosed in the Patent Literature 1 is configured, however, so as to apply the rotating magnetic field to the rotator through a side surface of the sample container. In other words, the rotating magnetic field is produced by electromagnet pairs or permanent magnet pairs arranged on a rotation plane of the rotator. In the former, the rotating magnetic field is produced when each pair of facing electromagnets arranged interposing the rotator is excited sequentially by giving different polarity on each electromagnet of the electromagnet pair. In the latter, a pair of permanent magnets, the permanent magnets being arranged interposing the rotator in a condition that the respective magnet in opposite position has a different polarity, is made to rotate in the rotation plane. Even in either configuration, it is necessary to arrange the plurality of the electromagnets or the permanent magnets (referred simply to as "magnet" hereinafter) on the same plane. Since the sample container is placed between the facing magnets, it is hard to reduce a distance between the magnets facing each other. Therefore, the viscosity measuring apparatus requires a relatively large area and dimensions, and a shape of the sample container for the measurement is limited because the sample container is arranged between the magnets facing each other.

At obtaining the temperature dependency of viscosity of the sample, it is necessary to perform the measurement keeping the sample liquid at a specific temperature. Under the configuration disclosed in the patent literature 1, however, it is difficult to arrange a temperature control system around the sample container only, so the temperature control system needs to be arranged around the whole apparatus. As described above, the dimensions of the viscosity measuring apparatus is relatively large, with the result that a large apparatus is required for the temperature control system. Additionally, since the dimensions to be subjected to the temperature control is large in such apparatus, the measurement for obtaining the temperature dependency takes very long time.

The present invention is suggested in view of the problems in the prior arts as described above, and has a purpose to provide a viscosity measuring apparatus that is downsized and has a comparative high degree of design freedom in the shape of the sample container.

Solution to Problem

The present invention employs under-mentioned technical means in order to achieve the above purpose. The viscosity measuring apparatus in the present invention comprises a sample container, a conductivity rotator, a magnet, a fluctuating magnetic field drive unit, and a viscosity detecting unit. The sample container contains a sample liquid. The conductivity rotator is immersed in the sample liquid in the sample container. The magnet is arranged at a specific distance from a rotation plane of the rotator in a direction of a rotating axis of the rotator so as to face the sample container. The magnet applies a magnetic field to the rotator from the outside of the sample container. The fluctuating magnetic field drive unit drives the magnet to apply the magnetic field fluctuating with time to the rotator. Induced current is excited in the rotator by the fluctuating magnetic field. A rotating torque is provided to the rotator by the Lorentz interaction between the induced current and the fluctuating magnetic field. In result, the rotator rotates in the rotation plane. The viscosity detecting unit obtains the viscosity of the sample liquid based on a rotating sate of the rotator and a time-fluctuating state of the fluctuating magnetic field. Besides, the magnet may consist of permanent magnet or electromagnet. In case of the permanent magnet, the fluctuating magnetic field is produced by a motion of the permanent magnet. In case of the electromagnet, the fluctuating magnetic field is produced by controlling the current to be applied to the electromagnet. As the fluctuating magnetic field to provide the rotating torque on the rotator, a rotating magnetic field can be employed.

In the viscosity measuring apparatus, the magnet does not surround the sample container, but arranged at the specific distance from the rotation plane of the rotator in the direction of the rotating axis of the rotator, so as to face to the sample container. Specifically, the magnet is placed at a side against the sample container, so that an occupied area (footprint) or dimensions of the apparatus can be significantly reduced in the present invention as compared with the conventional apparatus. In the configuration in this invention, it is possible to detect the viscosity of the sample liquid contained in an arbitrary shaped sample container. For instance, it is possible to continuously detect, on in-line, the viscosity of a liquid material or a liquid product flowing in a tube of a production line in a plant. The magnet is not arranged surrounding the sample container, so that a temperature control system can be arranged surrounding the sample container only. That is to say, it is possible to configure the viscosity measuring apparatus with the temperature control system that is more compact and controls the temperature in a short time than the conventional apparatus.

The above-mentioned viscosity measuring apparatus can employ a configuration that the magnet produces a magnetic field line parallel to the rotation plane of the rotator at the rotation plane. In the description, the means of "parallel" implies not only a perfectly parallel case but also a substantially parallel case. By such configuration, the rotating torque can be provided to the rotator with effect. For instance, it is possible to use the magnet having N pole and S pole consisting of belt-like regions being parallel mutually on a plane at a specific distance from the rotation plane of the rotator in the direction of the rotating axis of the rotator.

The viscosity measuring apparatus may further comprise a housing for storing the magnet. In this case, a wall surface of the housing is arranged between the sample container and the magnet. In the configuration, it is possible to easily keep a predetermined distance from the wall surface of the housing between the sample container and the magnet to the sample container. For instance, the sample container can be placed so as to contact with the wall surface of the housing between the sample container and the magnet. In such case, by setting a small distance between the magnet and the wall surface of the housing between the sample container and the magnet, the sample container can be placed very close to the magnet. That is to say, it is possible to apply the magnetic field to the rotator effectively. Besides, if the wall surface of the housing between the sample container and the magnet constitutes a vertically upward wall surface of the housing, it is very easy to set the sample container.

It is possible to employ the configuration that the wall surface of the housing between the sample container and the magnet has a fitting section for fitting to the sample container. In this case, if the bottom of the sample container is a curved surface, it is possible to easily set the sample container at a predetermined position. The wall surface of the housing between the sample container and the magnet may be a flat plane. In such case, it is easy to dispose a supporting member for setting the sample container at the predetermined position.

Advantageous Effects of Invention

According to the present invention, the magnet for producing the magnetic field is placed at a side against the sample container, so that the occupied area and dimensions of the apparatus can be reduced significantly as compared with the conventional apparatus. In addition, since the magnet for producing the magnetic field does not require to be arranged surrounding the sample container, it is possible to use an arbitrary shaped sample container. It is possible that an additional unit such as the temperature control system is arranged only surrounding the sample container with ease.

DESCRIPTION OF EMBODIMENTS

Embodiments of the present invention are explained in details hereinafter according to the drawings. In the undermentioned description, the viscosity measuring apparatus of the present invention is realized by producing a rotating magnetic field using permanent magnets.

Figure 1:
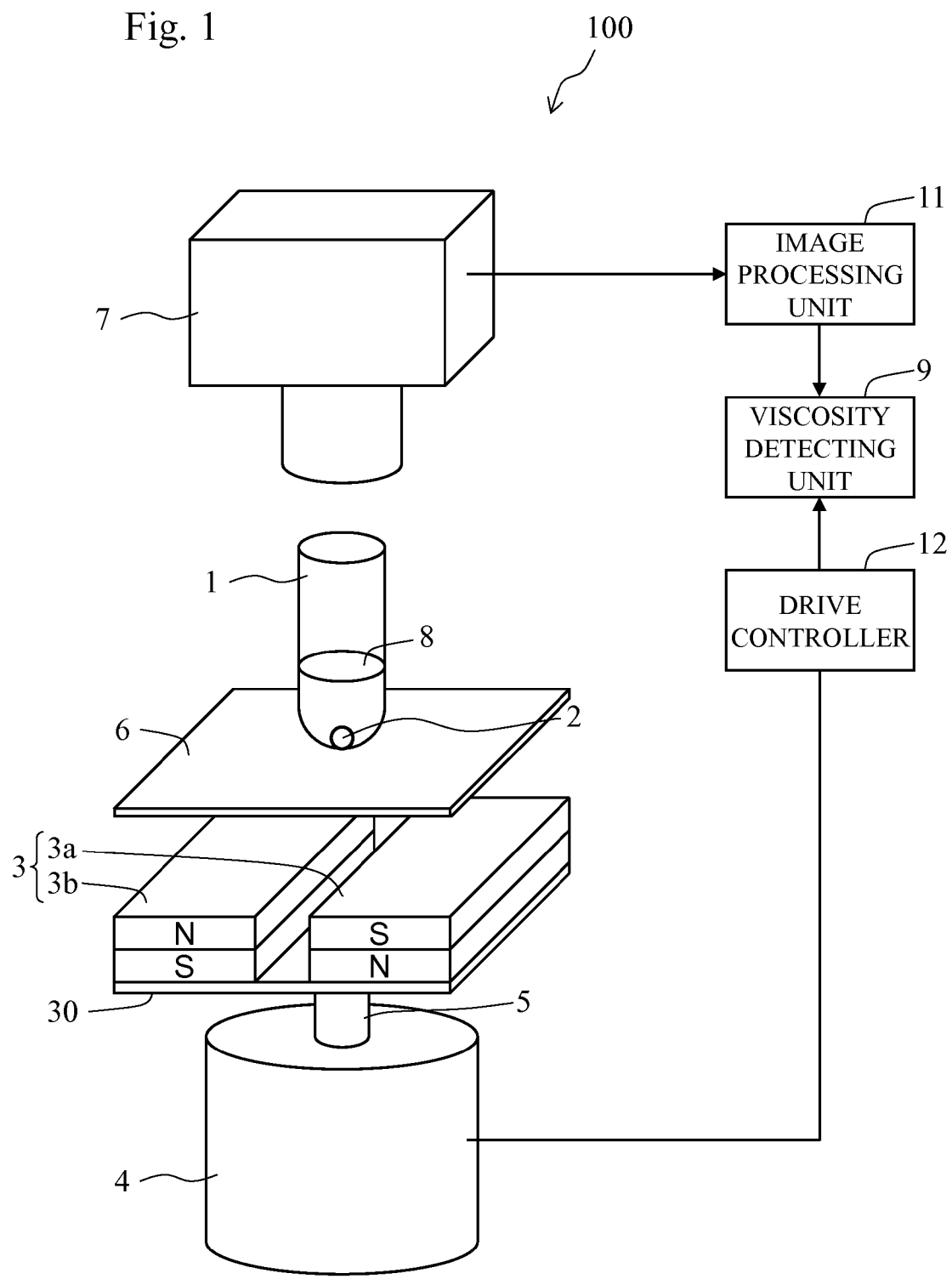
FIG. 1 is a schematic configuration diagram showing an overall configuration of a viscosity measuring apparatus in accordance with an embodiment of the present invention.

FIG. 1 is a schematic configuration diagram showing a configuration of the viscosity measuring apparatus in accordance with this embodiment. As shown in FIG. 1, the viscosity measuring apparatus 100 is provided with a sample container 1, a rotator 2, a magnet 3 (magnets 3a, 3b), a fluctuating magnetic field drive unit 4, and a viscosity detecting unit 9.

The sample container 1 contains a sample liquid 8 to be measured. A material of the sample container 1 is not limited in particular if the magnetic field is produced inside the container by the magnet 3. In FIG. 1, a quartz glass test tube, of which opening end is arranged in a vertically upward direction, is used as the sample container 1.

The rotator 2 is made of a conductivity material, and immersed in the sample liquid 8 in the sample container 1. A part of the rotator 2, which is in contact with the sample container 1, is desirable to have a convex curving surface. The rotator 2 in this embodiment has a radius smaller than a radius of curvature at a bottom of the test tube that is the sample container 1, and made of an aluminum sphere. The rotator 2 is placed in the sample container 1 so that a part or entire of the rotator 2 is sinking in the sample liquid 8. In FIG. 1, since the rotator 2 rotates around the vertical axis, a rotation plane of the rotator 2 becomes parallel to a top surface of the sample liquid 8 contained in the sample container 1.

The magnet 3, consisting of permanent magnet, is arranged below the sample container 1 so as to face the sample container 1, and applies a magnetic field to the rotator 2 from the outside of the sample container 1. In this embodiment, the magnet 3 comprises a magnet 3a with S pole facing the sample container 1 and a magnet 3b with N pole facing the sample container 1. A plane surface of the magnet 3a (S pole) facing the sample container 1 and a plane surface of the magnet 3b (N pole) facing the sample container 1 are arranged so as to be parallel with the rotation plane of the rotator 2.

The magnets 3a and 3b are in a belt-like shape in plain view and fixed on a rotating table 30 rotating within a plane parallel to the rotation plane of the rotator 2. The sample container 1 is set so that a rotating axis of the rotating table 30 is identical with a center axis of the test tube that is the sample container 1, and rectangular parallelepiped-shaped magnets 3a and 3b are symmetrically arranged with respect to a plane including the rotating axis. By arranging the magnets 3a and 3b in such manner, the magnet 3 produces a magnetic field line on the rotation plane of the rotator 2, the magnetic field line being parallel to the rotation plane of the rotator 2. It is not limited in particular in this embodiment that longitudinal sides of the magnets 3a and 3b are parallel to the above-mentioned plane including the rotating axis of the rotating table 30.

It is not limited in particular in the embodiment that a sample stage 6 is placed in contact with the sample container 1, and arranged between the magnet 3 and the sample container 1 so that a distance between the magnet 3 and the rotator 2 be always fixed. The sample stage 6 can use a material that does not prevent the magnet 3 from applying the magnetic field to the rotator 2, for example, like non-magnetic materials or thin magnetic materials. The upper surface of the sample stage 6 is parallel to the rotation plane of the rotator 2 and the rotation plane of the rotating table 30. Under such configuration, it is possible to arrange the magnet 3 close to the sample container 1 by reducing a distance between the sample stage 6 and the magnet 3. That is to say, it is possible to apply the magnetic field to the rotator 2 effectively.

The fluctuating magnetic field drive unit 4 drives the magnet 3 to apply the magnetic field that fluctuates in term of time to the rotator 2. The fluctuating magnetic field drive unit 4 in this embodiment includes a motor 4 having a rotation axis 5 arranged on the same axis as the rotating axis of the rotating table 30. Therefore, the fluctuating magnetic drive unit 4 in the embodiment gives the rotator 2 a rotating magnetic field as the fluctuating magnetic field.

The induced current is excited in the rotator 2 by the rotating magnetic field. By the Lorentz interaction between the induced current and the rotating magnetic field, the rotating torque is provided to the rotator 2, and then the rotator 2 rotates. It is not limited in particular that this embodiment shows an example that the rotating axis of the rotator 2 is identical with the rotating axis of the rotating table 30.

The viscosity detecting unit 9 obtains the viscosity of the sample liquid 8 based on a rotating state of the rotator 2 and a time-fluctuating state of the fluctuating magnetic field. The rotating state of the rotator 2 can be obtained by a CCD (Charge Coupled Device) camera 7 provided over the sample container 1. An image processing unit 11 processes images showing the rotating state of the rotator 2 obtained by the CCD camera 7, and the number of rotations of the rotator 2 can be calculated. For instance, the image processing unit 11 counts the number of rotations of the rotator 2 by detecting a mark put on a top of the rotator 2.

The time-fluctuating state of the fluctuating magnetic field can be obtained as the number of rotations of the rotating magnetic field. The number of rotations of the rotating magnetic field is identical with the number of rotations of the rotation driving axis 5. Accordingly, the number of rotations of the rotating magnetic field can be obtained from the number of rotations of the motor of the fluctuating magnetic field drive unit 4 or the number of rotations of the rotating table 30. Although the number of rotations of the rotating magnetic field can be obtained by means of the image processing in the same manner as the number of rotations of the rotator 2, it is configured in this embodiment that the number of rotations of the rotating magnetic field is obtained from a drive controller 12 for controlling the number of rotations of the fluctuating magnetic field drive unit 4.

The viscosity detecting unit 9 obtains the number of rotations of the rotator 2 and the number of rotations of the rotating magnetic field from the image processing unit 11 and the drive controller 12 respectively, and calculates the viscosity of the sample liquid 8 based on the obtained numbers of rotations of the rotator 2 and the rotating magnetic field. For the calculation of the viscosity, the lag in the rotating speed of the rotator 2 to the rotating speed of the rotating magnetic field, which is caused by the viscosity of the sample liquid, is used. That is to say, based on a relation of the rotating speed of the rotator 2 and the difference between the rotating speed of the rotator 2 and the rotating speed of the rotating magnetic field, the relation can be expressed by a liner equation, a slope of the linear equation is defined as the viscosity. The viscosity of the sample liquid 8 can be found as a product of the viscosity of a standard sample (a sample liquid with known viscosity) and a ratio of the slope relating to the sample liquid 8 and the previously obtained slope relating to the standard sample. This viscosity calculation method is same as conventional method, which is not explained here in details.

Regarding the above-mentioned configuration, the viscosity detecting unit 9, the image processing unit 11 and the drive controller 12 can be realized by, for example, an exclusive-use calculation circuit, or hardware having a processor and memories such as RAM (Random Access Memory) or ROM (Read Only Memory), etc. and software stored in the memories and operating on the processor.

In the viscosity measuring apparatus 100, the magnet 3 does not surround a periphery of the sample container 1 but arranged at a side against the sample container 1. Accordingly, it is possible to significantly reduce an occupied area (footprint) or dimensions of the apparatus as compared with the conventional apparatus. Since the magnet 3 is not arranged surrounding the periphery of the sample container 1, even if the sample liquid is contained in the container in any shape, the viscosity can be obtained. In addition, since the magnet 3 is not arranged surrounding the periphery of the sample container 1, the temperature control system can be arranged surrounding only the periphery of the sample container. Namely, the viscosity measuring apparatus with the temperature control system can be realized as an apparatus that is compact and can control the temperature in a short time, as compared with the conventional apparatus.

Figure 2A:
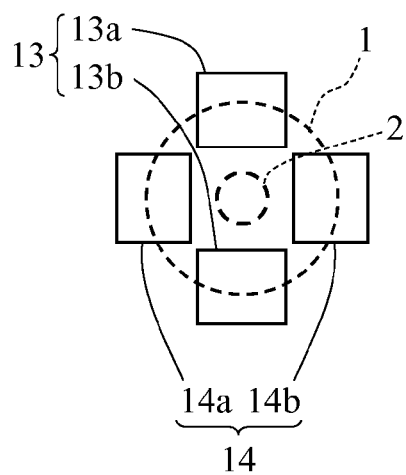
FIG. 2(a) and FIG. 2(b) are schematic configuration diagrams showing variations of the viscosity measuring apparatus in accordance with an embodiment of the present invention.
Figure 2B:
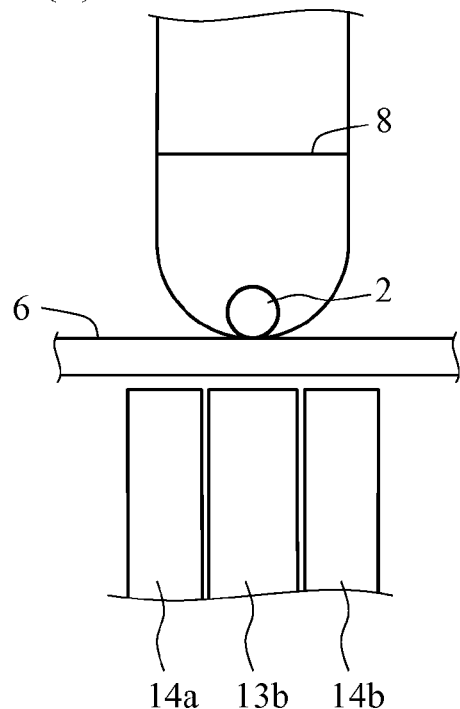

Besides, the magnet 3 may consist of electromagnet. FIG. 2(a) and FIG. 2(b) are schematic configuration diagrams showing a configuration wherein an electromagnet is used as the magnet giving the rotator 2 the fluctuating magnetic field. FIG. 2(a) is a plane view, and FIG. 2(b) is an elevation view. In FIG. 2(a), the external shapes of the sample container 1 and the rotator 2 are illustrated by a broken line.

As shown in FIGS. 2(a) and 2(b), two pairs of the electromagnets 13 and 14 are arranged below the sample container 1 so as to face the sample container 1. The electromagnet pair 13 is a pair of electromagnets 13a and 13b arranged interposing the rotating axis of the rotator 2 so as to face each other. In the same manner, the electromagnet pair 14 is a pair of electromagnets 14a and 14b arranged interposing the rotating axis of the rotator 2 so as to face each other. As shown in FIG. 2(a), this embodiment indicates in plane view that the arrangement direction of the electromagnet pair 13 is perpendicular to the arrangement direction of the electromagnet pair 14.

The electromagnets 13a, 13b, 14a, and 14b are wound with coil so as to produce the magnetic field along the rotating axis of the rotator 2 (the center axis of the test tube that is the sample container 1), and a single magnetic pole is produced on each surface (top surface) of the electromagnets 13a, 13b, 14a and 14b that face to the sample container 1. The electromagnets constituting a pair of the electromagnets are applied with the current at the same time. When the electromagnets constituting a pair of the electromagnets are applied with the current, the magnetic field having the opposite polarity is produced on each electromagnet. For instance, when the current is applied on the electromagnet pair 13, if the surface of the electromagnet 13a facing the sample container 1 is N pole, the surface of the electromagnet 13b facing the sample container 1 becomes S pole.

In this configuration, the fluctuating magnetic field drive unit 4 includes a current source for controlling the current to be applied to respective electromagnet pairs 13 and 14. The drive controller 12 controls the timing of applying the current on the respective electromagnet pairs 13 and 14. The drive controller 12 applies the driving current, which shows a various fluctuation with time, on the electromagnet pairs 13 and 14, respectively. For instance, when a sine wave current oscillating at frequency f, $I=I_0 \sin(2\pi ft)$, is applied on the electromagnet pair 13, the electromagnet pair 14 is applied with a eosin wave current oscillating at frequency f, $I=I_0 \cos(2\pi ft)$. Here, $I_0$ denotes a constant, and t denotes time. By this configuration, the rotating magnetic field can be produced in the same manner as the configuration for rotating the rotating table 30.

The number of rotations of rotator 2 can be detected by any arbitrary method not only the above method. For instance, it is possible to optically detect the change of reflection and interference pattern due to by the rotation by irradiating the laser beams to the rotator 2. The number of rotations of the rotating magnetic field can be detected in the same manner.

Figure 3:
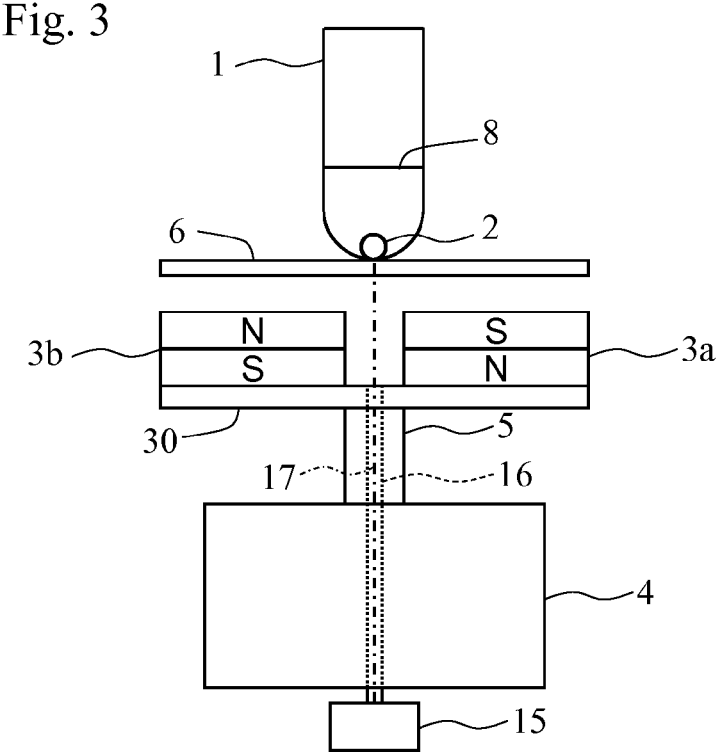
FIG. 3 is a schematic configuration diagram showing a variation of the viscosity measuring apparatus in accordance with an embodiment of the present invention.
Figure 4:
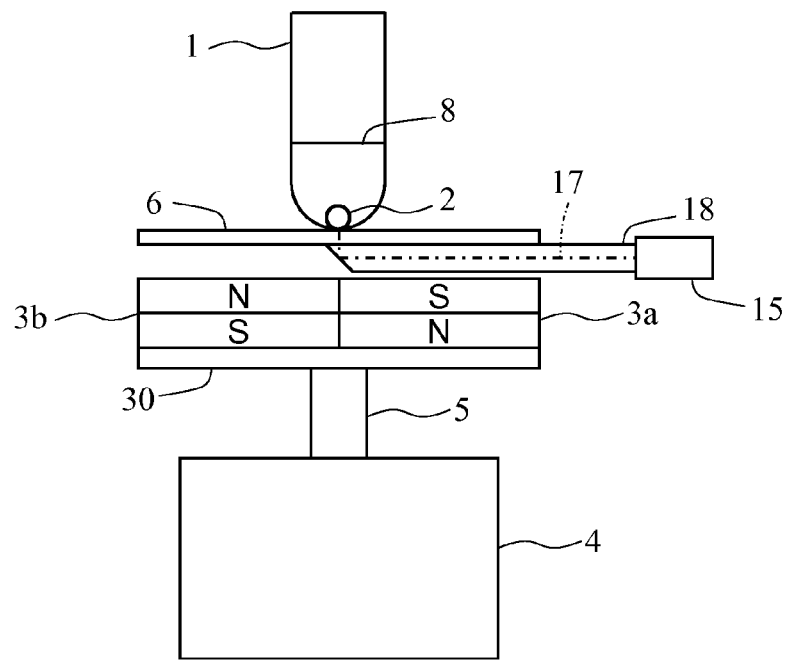
FIG. 4 is a schematic configuration diagram showing a variation of the viscosity measuring apparatus in accordance with an embodiment of the present invention.

In FIG. 1, the number of rotations of the rotator 2 is detected from an upper side of the sample container 1, but the number of rotations may be detected from an under side of the sample container 1, that is, from a side of the sample stage 6. FIG. 3 and FIG. 4 are schematic configuration diagrams showing a configuration for detecting the number of rotations of the rotator 2 from the side of the sample stage 6. In FIG. 3 and FIG. 4, the configuration using the permanent magnets explained in accordance with FIG. 1 is employed as a configuration for producing the rotating magnetic field. Therefore, the elements that are provided with the effects same as the elements in FIG. 1 are given the same reference signs, which are not explained in details here.

In FIG. 3, the rotation driving axis 5 of the motor that is the fluctuating magnetic field driving unit 4 is hollow inside, and an optical fiber 16 that works as a light guide is provided to the hollow section. An end of the optical fiber 16 is exposed on a surface of the rotating table 30 so as to face the rotator 2 rotating in the sample container 1. The other end of the optical fiber 16 is connected to a rotation detecting unit 15 for detecting the number of rotations that is arranged in an opposite position to the rotating table 30 interposing the motor that is the fluctuating magnetic field driving unit 4. It is not limited in particular that the rotation detecting unit 15 is provided with a light emitting unit emitting the laser beam 17 to the rotator 2 via the optical fiber 16, and a light receiving unit receiving the laser beam 17 reflected by the rotating rotator 2 via the optical fiber 16. The rotation detecting unit 15 obtains the number of rotations by the change of reflection and interference pattern due to the rotation of the rotator 2 at the light receiving unit. In such configuration, a part of the sample stage 6 and the sample container 1 that exist on a path of the laser beam 17 is made of translucent material.

In FIG. 4, a light guide 18 is provided on a side of the sample stage 6 facing the fluctuating magnetic field drive unit 4. The light guide 18 is arranged between the sample stage 6 and the magnet 3, in a horizontal direction from directly below the rotator 2 rotating in the sample container 1 to the outward end of the rotating table 30, in a plane view. The outward end of the rotating table 30 is connected to the rotation detecting unit 15. The laser beam 17 is emitted from the light emitting unit of the rotation detecting unit 15, and propagated through the light guide 18 in the horizontal direction. In order to reflect the laser beam 17 toward the rotator 2 (the vertical direction), a reflecting surface is provided directly below the rotator 2 rotating in the sample container 1. The reflecting surface reflects the laser beam 17 reflected by the rotating rotator 2 toward the light receiving unit of the rotation detecting unit 15. The rotation detecting unit 15 obtains the number of rotations by detecting the change of reflection and interference pattern due to the rotation of the rotator 2 at the light receiving unit. In this configuration, at least the parts of the sample stage 6 and the sample container 1 that exist on a path of the laser beam 17 is made of translucent material, too. This configuration may be realized by arranging the magnets 3a and 3b contacting each other on the rotating table 30, as shown in FIG. 4. Such arrangement is very effective at reducing the footprint of the viscosity measuring apparatus.

Figure 5:
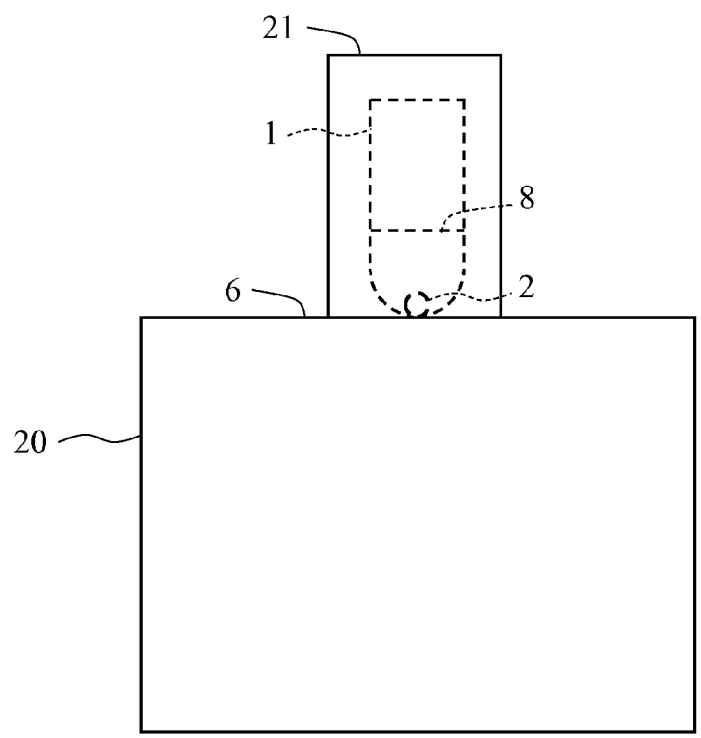
FIG. 5 is a schematic configuration diagram showing a variation of the viscosity measuring apparatus in accordance with an embodiment of the present invention.
Figure 6:
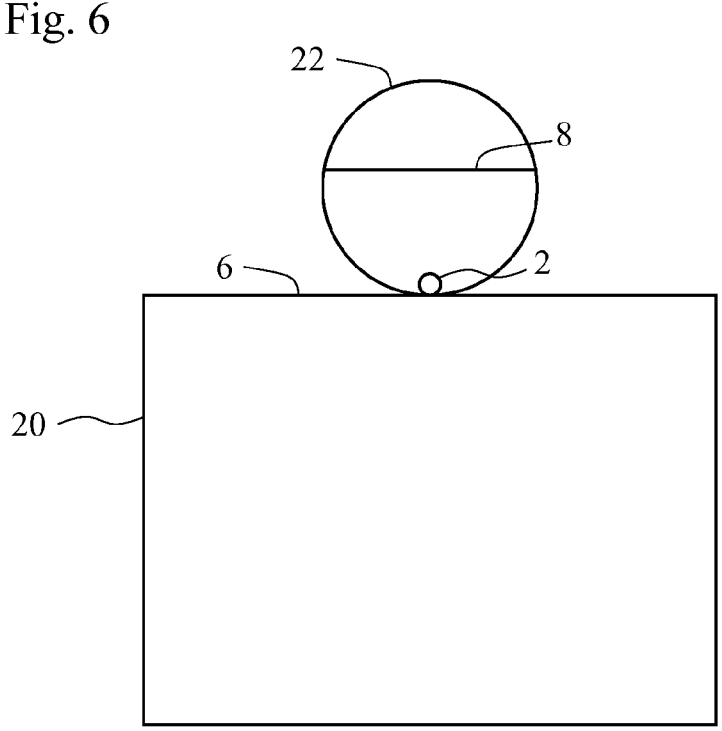
FIG. 6 is a schematic configuration diagram showing a variation of the viscosity measuring apparatus in accordance with an embodiment of the present invention.

In the above-mentioned configuration for detecting the number of rotations of the rotator 2 from below the sample container 1, all the members except the sample container 1 can be arranged on a side of the sample stage 6 opposite to the sample container 1. That is to say, the viscosity can be measured only from one side of the sample container 1. Therefore, as shown in FIG. 5, for example, if the sample container 1 is surrounded by a temperature control container 21 having the temperature control system, the viscosity of the sample liquid 8 can be obtained. As shown in FIG. 6, for example, it is possible in a plant to continuously obtain, on in-line, the viscosity of a liquid material or a liquid product flowing in a tube 22 provided to the production line. Besides, at measuring the viscosity of the sample liquid 8 flowing through the tube 22, it is desirable that a rotating position of the rotator 2 be kept in a fixed position by providing the inside of the tube 22 with a concave. In FIG. 5 and FIG. 6, the magnet 3, the rotating table 30 and the fluctuating magnetic field drive unit 4 are contained in a housing 20. In this case, the sample stage 6 comprises all or a part of a wall (upper surface) of the housing 20 facing the sample container 1.

The above description has related to an example that the surface of the sample stage 6 in contact with the sample container 1 is flat plane. When the surface of the sample stage 6 in contact with the sample container 1 is flat plane, in case of using a plurality of sample containers having different shapes, any supporting member fitting to each sample container can be arranged on the sample stage 6. In result, even if the plurality of sample containers having different shapes is used, the rotator 2 in each sample container can be set to a predetermined position.

Figure 7A:
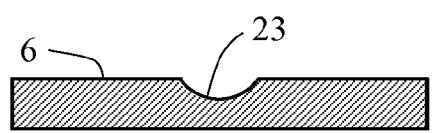
FIG. 7(a) and FIG. 7(b) are schematic cross-sectional diagrams showing a variation of the viscosity measuring apparatus in accordance with an embodiment of the present invention.
Figure 7B:
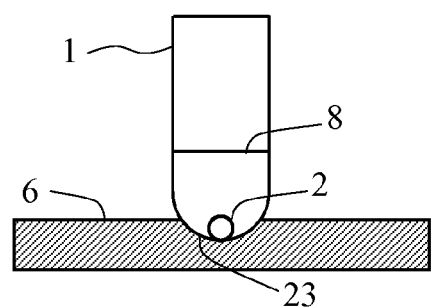

It is not indispensable that the surface of the sample stage 6 in contact with the sample container 1 should be a flat plane surface. FIG. 7(a) and FIG. 7(b) show another example of the sample stage 6. FIG. 7(a) is a diagram showing a state that the sample container 1 is not placed thereon, and FIG. 7(b) is a diagram showing a state that the sample container 1 is placed thereon. As shown in FIG. 7(a) and FIG. 7(b), the surface of the sample stage 6 in contact with the sample container 1 is provided with a fitting section 23 fitting the sample container 1. According to the configuration provided with the fitting section 23 fitting the contacting surface of the sample container 1, it is easy to set the rotator 2 of the sample container 1 to the predetermined position, even if the bottom surface of the sample container 1 is curved.

As described above, the present invention is configured that the magnet for producing the fluctuating magnetic field are arranged on one side against the sample container. Therefore, the occupied area and dimensions of the apparatus can be reduced significantly. Since there is no necessity to arrange the magnets for producing the fluctuating magnetic field surrounding the sample container, it is possible to use any arbitrary shaped sample container. Additionally, various additional units including the temperature control system can be easily arranged surrounding the sample container.

The above-mentioned embodiments do not limit the technical range of the present invention, and in addition to the examples described above, various modification and application are available within a range of the present invention. For example, the above-mentioned embodiment shows a configuration that two magnetic poles are disposed facing the sample container, but the position of the magnet may be configured in arbitrary, if it is possible to produce the fluctuating magnetic field for providing the rotating torque to the rotator. That is to say, there may be only one magnetic pole that exists at the position facing the sample container.

The above-mentioned embodiments have explained an example that the rotation plane of the rotator is horizontal, but the rotation plane of the rotator can be set arbitrarily within the range providing the effect of the present invention.

INDUSTRIAL APPLICABILITY

In the present invention, the degree of design freedom in the shape of the sample container is quite high, and the dimensions of the apparatus can be downsized, so that the viscosity measuring apparatus of the present invention has a high applicability.

REFERENCE SIGNS LIST

100 Viscosity measuring apparatus
1 Sample container
2 Rotator
3, 13, 14 Magnet (Magnet pair)
3a, 3b Permanent magnet
13a, 13b, 14a, 14b Electromagnet
4 Fluctuating magnetic filed drive unit
5 Rotation driving axis
6 Sample stage
7 CCD camera
8 Sample liquid
9 Viscosity detecting unit
15 Rotation detecting unit
20 Housing
21 Temperature control container
22 Tube

The invention claimed is:

1. A viscosity measuring apparatus for measuring the viscosity of a sample liquid contained in a sample container and having a conductivity rotator immersed in the sample liquid, comprising:
 a magnet arranged at a specific distance from a rotation plane of the rotator in a direction of a rotating axis of the rotator so as to face the sample container and applying a magnetic field to the rotator from an outside of the sample container;
 a fluctuating magnetic field drive unit configured to drive the magnet to apply the magnetic field fluctuating with time to the rotator, excite induced current in the rotator, provide the rotator with a rotating torque by the Lorentz interaction between the induced current and the fluctuating magnetic field, and rotate the rotator in the rotation plane;
 a rotation detecting unit including an optical systems provided to the outside of the sample container and configured to detect the number of rotations of the rotator;
 a drive controller configured to apply the number of rotations of the fluctuating magnetic field drive unit; and
 a viscosity detecting unit configured to obtain the viscosity of the sample liquid based on the number of rotations of the rotator obtained by the rotation detecting unit and the number of rotations obtained by the drive controller.

2. The viscosity measuring apparatus according to claim 1, wherein the rotation detecting unit is arranged adjacent, under or over the sample container.

3. The viscosity measuring apparatus according to claim 1, wherein the magnet produces a magnetic field line parallel to the rotation plane of the rotator at the rotation plane.

4. The viscosity measuring apparatus according to claim 3, the magnet has N pole and S pole consisting of belt-like regions being parallel mutually on a plane at a specific distance from the rotation plane of the rotator in the direction of the rotating axis of the rotator.

5. The viscosity measuring apparatus according to claim 3, further comprising a housing for storing the magnet, wherein a wall surface of the housing is arranged between the sample container and the magnet.

6. The viscosity measuring apparatus according to claim 1, the magnet has N pole and S pole consisting of belt-like regions being parallel mutually on a plane at a specific distance from the rotation plane of the rotator in the direction of the rotating axis of the rotator.

7. The viscosity measuring apparatus according to claim 6, further comprising a housing for storing the magnet, wherein a wall surface of the housing is arranged between the sample container and the magnet.

8. The viscosity measuring apparatus according to claim 1, further comprising a housing for storing the magnet, wherein a wall surface of the housing is arranged between the sample container and the magnet.

9. The viscosity measuring apparatus according to claim 8, wherein the wall surface of the housing between the sample container and the magnet has a fitting section for fitting to the sample container.

10. The viscosity measuring apparatus according to claim 8, wherein the wall surface of the housing between the sample container and the magnet is a flat plane.

11. The viscosity measuring apparatus according to claim 8, the wall surface of the housing between the sample container and the magnet constitutes a vertically upward wall surface of the housing.

12. The viscosity measuring apparatus according to claim 11, wherein the wall surface of the housing between the sample container and the magnet has a fitting section for fitting to the sample container.

13. The viscosity measuring apparatus according to claim 11, wherein the wall surface of the housing between the sample container and the magnet is a flat plane.

14. The viscosity measuring apparatus according to claim 8, wherein the sample container is placed so as to contact with the Wall surface of the housing between the sample container and the magnet.

15. The viscosity measuring apparatus according to claim 14, the wall surface of the housing between the sample container and the magnet constitutes a vertically upward wall surface of the housing.

16. The viscosity measuring apparatus according to claim 14, wherein the wall surface of the housing between the sample container and the magnet has a fitting section for fitting to the sample container.

17. The viscosity measuring apparatus according to claim 14, wherein the wall surface of the housing between the sample container and the magnet is a flat plane.

* * * * *